(12) United States Patent
Chee

(10) Patent No.: US 6,368,799 B1
(45) Date of Patent: Apr. 9, 2002

(54) METHOD TO DETECT GENE POLYMORPHISMS AND MONITOR ALLELIC EXPRESSION EMPLOYING A PROBE ARRAY

(75) Inventor: Mark Chee, Del Mar, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/445,734

(22) PCT Filed: Jun. 11, 1998

(86) PCT No.: PCT/US98/12442

§ 371 Date: Mar. 14, 2000

§ 102(e) Date: Mar. 14, 2000

(87) PCT Pub. No.: WO98/56954

PCT Pub. Date: Dec. 17, 1998

Related U.S. Application Data

(60) Provisional application No. 60/049,612, filed on Jun. 13, 1997.

(51) Int. Cl.[7] ............ C12Q 1/68; C12P 19/34; C12M 1/34; C07H 21/04; C07H 21/00
(52) U.S. Cl. ............ 435/6; 435/911; 435/91.2; 435/283.1; 435/285.1; 435/287.2; 536/221; 536/23.1; 536/29.3; 536/24.81; 536/24.32; 536/24.33
(58) Field of Search .......... 435/6, 91.1, 91.2, 435/283.1, 285.1; 536/23.1, 24.2, 24.3, 24.31, 24.32, 24.33

(56) References Cited

U.S. PATENT DOCUMENTS

| | | | | |
|---|---|---|---|---|
| 5,487,985 A | * | 1/1996 | McClelland et al. | 435/91.2 |
| 5,709,998 A | * | 1/1998 | Kinzler et al. | 435/6 |
| 5,858,659 A | * | 1/1999 | Sapolsky et al. | 435/6 |
| 6,048,689 A | * | 4/2000 | Murphy et al. | 435/6 |

OTHER PUBLICATIONS

Chee et al Science vol. 274. no. 5287 1996 pp. 610–614.*

* cited by examiner

*Primary Examiner*—Jeffrey Siew
(74) *Attorney, Agent, or Firm*—Townsend and Townsend and Crew LLP

(57) ABSTRACT

The invention provides methods of monitoring expression levels of different polymorphic forms of a gene. Such methods entail analyzing genomic DNA from an individual to determine the presence of heterozygous polymorphic forms at a polymorphic site within a transcribed sequence of a gene of interest. RNA from a tissue of the individual in which the gene is expressed is then analyzed to determine relative proportions of polymorphic forms in transcript of the gene. Having identified alleles of a gene that are expressed at different levels, the alleles can be further analyzed to locate a second polymorphism that has a causative role in the different expression levels. The methods are amenable to analyzing large collections of genes simultaneously using arrays of immobilized probes.

11 Claims, No Drawings

METHOD TO DETECT GENE POLYMORPHISMS AND MONITOR ALLELIC EXPRESSION EMPLOYING A PROBE ARRAY

CROSS-REFERENCE TO RELATED APPLICATIONS

The present application derives priority from USSN 60/049,612 filed Jun. 13, 1997, which is incorporated by reference in its entirety for all purposes.

BACKGROUND

The genomes of all organisms undergo spontaneous mutation in the course of their continuing evolution generating variant forms of progenitor sequences (Gusella, Ann. Rev. Biochem. 55, 831–854 (1986)). The variant form may confer an evolutionary advantage or disadvantage relative to a progenitor form or may be neutral. In some instances, a variant form confers a lethal disadvantage and is not transmitted to subsequent generations of the organism. In other instances, a variant form confers an evolutionary advantage to the species and is eventually incorporated into the DNA of many or most members of the species and effectively becomes the progenitor form. In many instances, both progenitor and variant form(s) survive and co-exist in a species population. The coexistence of multiple forms of a sequence gives rise to polymorphisms.

Several different types of polymorphism have been reported. A restriction fragment length polymorphism (RFLP) means a variation in DNA sequence that alters the length of a restriction fragment as described in Botstein et al., *Am. J. Hum. Genet.* 32, 314–331 (1980). Other polymorphisms take the form of short tandem repeats (STRs) that include tandem di-, tri- and tetra-nucleotide repeated motifs. Some polymorphisms take the form of single nucleotide variations between individuals of the same species. Such polymorphisms are far more frequent than RFLPs, STRs and VNTRs. Single nucleotide polymorphisms can occur anywhere in protein-coding sequences, intronic sequences, regulatory sequences, or intergenomic regions.

Many polymorphisms probably have little or no phenotypic effect. Some polymorphisms, principally those occurring within coding sequences, are known to be the direct cause of serious genetic diseases, such as sickle cell anemia. Polymorphisms occurring within a coding sequence typically exert their phenotypic effect by leading to a truncated or altered expression product. Still other polymorphisms, particularly those in promoter regions and other regulatory sequences, may influence a range of disease-susceptibility, behavioral and other phenotypic traits through their effect on gene expression levels. That is, such polymorphisms may lead to increased or decreased levels of gene expression without necessarily affecting the nature of the expression product.

SUMMARY OF THE INVENTION

The invention provides methods of monitoring expression levels of different polymorphic forms of a gene. Such methods entail analyzing genomic DNA from an individual to determine the presence of heterozygous polymorphic forms at a polymorphic site within a transcribed sequence of a gene of interest. RNA from a tissue of the individual in which the gene is expressed is then analyzed to determine relative proportions of polymorphic forms in transcript of the gene.

In some methods, genomic DNA is analyzed by amplifying a segment of genomic DNA from a sample and hybridizing the amplified genomic DNA to an array of immobilized probes. In some methods the array used for analyzing genomic DNA comprises a first probe group comprising one or more probes exactly complementary to a first polymorphic form of the gene and a second probe group comprising one or more probes exactly complementary to a second polymorphic form of the gene. In some methods, RNA is analyzed by reverse transcribing and amplifying mRNA expressed from the gene to produce an amplified nucleic acid and hybridizing the amplified nucleic acid to an array of immobilized probes. In some such methods, the amplified nucleic acid is cDNA. In some methods, the array of immobilized probes for analyzing RNA comprises a first probe group comprising one or more probes exactly complementary to a first polymorphic form of the gene, a second probe group comprising one or more probes exactly complementary to a second polymorphic form of the gene.

In some method, genomic DNA and the RNA are analyzed by hybridizing the genomic DNA or an amplification product thereof, and the RNA or an amplification product thereof, to the same array of immobilized probes comprising a first probe group comprising one or more probes exactly complementary to a first polymorphic form of the gene, and a second probe group comprising one or more probes exactly complementary to a second polymorphic form of the gene. In some methods, the genomic DNA, or amplification product, and the RNA, or amplification product, bear different labels and are hybridized simultaneously to the array.

Some methods further comprise comparing a genomic DNA hybridization intensity of the first probe group to the second group to determine a genomic hybridization ratio, and comparing an RNA hybridization intensity of the first group to the second group to determine an RNA hybridization ratio, whereby a difference in the genomic DNA and RNA ratios indicates that the polymorphic forms of the gene are expressed at different levels in the individual.

Some methods further comprise sequencing a nontranscribed region of the gene to identify a second polymorphic site in a promoter or enhancer region of the gene.

The invention further provides methods of monitoring expression levels of different polymorphic forms of a collection of genes. In such methods, genomic DNA, or an amplification product thereof from an individual is hybridized to an array of immobilized probes comprising a subarray of probes for each gene in the collection, wherein each subarray comprises a first group of one or more probes exactly complementary to a first polymorphic form of the gene and a second group of one or more probes exactly complementary to a second polymorphic form of the gene. The relative hybridization of the first and second group of probes to the genomic DNA or amplification product thereof are analyzed for each subarray to identify heterozygous genes in the individual. RNA or an amplification product thereof from the individual is hybridized to the array of immobilized probes. The hybridization intensities of the first and second groups of probes to the RNA or amplification product are compared to identify a subset of the heterozygous genes for which different polymorphic forms are expressed at different levels. Such methods can be performed to screen large collections of genes, e.g., 100, 1000, or 100,000. Some such methods further comprise sequencing a nontranscribed region of a gene in the subset to identify a further polymorphism in a promoter, enhancer or intronic sequence of the gene.

DEFINITIONS

A nucleic acid is a deoxyribonucleotide or ribonucleotide polymer in either single-or double-stranded form, including known analogs of natural nucleotides unless otherwise indicated.

An oligonucleotide is a single-stranded nucleic acid ranging in length from 2 to about 500 bases. Oligonucleotides are often synthetic but can also be produced from naturally occurring polynucleotides.

A probe is an oligonucleotide capable of binding to a target nucleic acid of complementary sequence through one or more types of chemical bonds, usually through complementary base pairing, usually through hydrogen bond formation. Oligonucleotides probes are often 10–50 or 15–30 bases long. An oligonucleotide probe may include natural (i.e. A, G, C, or T) or modified bases (7-deazaguanosine, inosine, etc.). In addition, the bases in oligonucleotide probe may be joined by a linkage other than a phosphodiester bond, so long as it does not interfere with hybridization. Thus, oligonucleotide probes may be peptide nucleic acids in which the constituent bases are joined by peptide bonds rather than phosphodiester linkages.

Specific hybridization refers to the binding, duplexing, or hybridizing of a molecule only to a particular nucleotide sequence under stringent conditions when that sequence is present in a complex mixture (e.g., total cellular) DNA or RNA. Stringent conditions are conditions under which a probe will hybridize to its target subsequence, but to no other sequences. Stringent conditions are sequence-dependent and are different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions include a salt concentration of at least about 0.01 to 1.0 M Na ion concentration (or other salts) at pH 7.0 to 8.3 and the temperature is at least about 30° C. for short probes (e.g., 10 to 50 nucleotides). Stringent conditions can also be achieved with the addition of destabilizing agents such as formamide. For example, conditions of 5×SSPE (750 mM NaCl, 50 mM NaPhosphate, 5 mM EDTA, pH 7.4) and a temperature of 25–30° C. are suitable for allele-specific probe hybridizations.

A perfectly matched probe has a sequence perfectly complementary to a particular target sequence. The test probe is typically perfectly complementary to a portion (subsequence) of the target sequence. The term "mismatch probe" refer to probes whose sequence is deliberately selected not to be perfectly complementary to a particular target sequence. Although the mismatch(es) may be located anywhere in the mismatch probe, terminal mismatches are less desirable as a terminal mismatch is less likely to prevent hybridization of the target sequence. Thus, probes are often designed to have the mismatch located at or near the center of the probe such that the mismatch is most likely to destabilize the duplex with the target sequence under the test hybridization conditions.

Transcriptions levels can be quantified absolutely or relatively. Absolute quantification can be accomplished by inclusion of known concentration(s) of one or more target nucleic acids (e.g. control nucleic acids such as Bio B or with known amounts the target nucleic acids themselves) and referencing the hybridization intensity of unknowns with the known target nucleic acids (e.g. through generation of a standard curve). Alternatively, relative quantification can be accomplished by comparison of hybridization signals between two or more polymorphic forms of a transcript.

A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as a the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A single nucleotide polymorphism (SNP) occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

DESCRIPTION

I. General

A substantial number of polymorphic sites in humans and other species have been described in the published literature, and many other polymorphic sites in human genomic DNA are described in commonly owned copending patent applications, such as PCT/US98/04571, filed Mar. 5, 1998 (incorporated by reference in their entirety for all purposes). The genomic locations of these sites are known, as is the nature of the polymorphic forms occurring at the sites. Many of the known polymorphic sites occur within so-called expressed sequence tags and are therefore represented in the transcript of genomic DNA, as well as genomic DNA itself. The present invention uses polymorphisms within the transcribed region of a gene as a means to monitor the relative expression of different allelic forms of the gene. Having identified alleles of a gene that are expressed at different levels, the alleles can be further analyzed to locate a second polymorphism that has a causative role in the different expression levels. Often, the causative polymorphism is found outside the coding sequence of a gene; for example, in a promoter, other regulatory sequence or an intronic sequence.

In the present methods, nucleic acid samples from individuals are characterized at both the genomic and transcriptional levels. The genomic analysis screens genomic DNA from an individual to identify one or more genes that are heterozygous for a polymorphism occurring within a transcribed region of a gene. RNA from the individual is then analyzed to determine the relative levels of polymorphic forms in the transcript of the heterozygous genes identified by the genomic analysis. If the levels of polymorphic forms in the transcript of a gene differ significantly from each other, further analysis is performed to identify the cause of the different levels. It is possible that the polymorphism within the transcript that is used for monitoring expression levels may itself affect expression levels. However, it is more likely that the difference in expression levels stems from another polymorphic difference between the alleles. Such polymorphisms are particularly likely to reside in promoter sequences, enhancers, intronic splice sites, or other regulatory sequences.

II. Analyzing Polymorphic Forms at the Genomic Level

Strategies for identification and detection of polymorphisms are described in commonly owned USSN 08/831,159, EP 730,663, EP 717,113, and PCT US97/02102, filed Feb. 7, 1997 (incorporated by reference in their entirety for all purposes). The present methods usually employ precharacterized polymorphisms. That is, the genotyping required by the present methods is usually performed after the location and nature of polymorphic forms present at a site have already been determined. The availability of this information allows sets of probes to be designed for specific identification of the known polymorphic forms.

In the simplest form of analysis, a biallelic polymorphism forms can be characterized using a pair of allele specific probes respectively hybridizing to the two polymorphic forms. However, analysis is more accurate using specialized arrays of probes tiled based on the respective polymorphic forms. Tiling refers to the use of groups of related immobilized probes, some of which show perfect complementarity to a reference sequence and others of which show mismatches from the reference sequence (see EP 730,663). A typically array for analyzing a known biallelic single nucleotide polymorphism contains two group of probes tiled based on two reference sequences constituting the respective polymorphic forms.

The first group of probes includes at least a first set of one or more probes which span the polymorphic site and are exactly complementary to one of the polymorphic forms. The group of probes can also contain second, third and fourth additional sets of probes, which contain probes identical to probes in the first probe set except at one position referred to as an interrogation position. When such a probe group is hybridized with the polymorphic form constituting the reference sequence, all probes in the first probe show perfect hybridization and all of the probes in the other probe sets show background hybridization levels due to mismatches.

When such a probe group is hybridized with the other polymorphic form, a different pattern is obtained. That is, all but one probes in the array show a mismatch to the target and produce only background hybridization. The one probe that shows perfect hybridization is a probe from the second, third or fourth probe sets whose interrogation position aligns with the polymorphic site and is occupied by a base complementary to the other polymorphic form.

When the probe group is hybridized with a heterozygous sample in which both polymorphic forms are present, the patterns for the homozygous polymorphic forms are superimposed. Thus, the probe group shows distinct and characteristic hybridization patterns depending on which polymorphic forms are present and whether an individual is homozygous or heterozygous.

Typically, an array also contains a second group of probes tiled using the same principles as the first group but with a reference sequence constituting the other polymorphic form. That is, the first probe set in the second group spans the polymorphic site and shows perfect complementary to the other polymorphic form. Hybridization of the second probe group to homozygous or heterozygous target sequences yields a mirror image of hybridization patterns from the first group. By analyzing the hybridization patterns from both probe groups, one can determine with a high accuracy which polymorphic form(s) are present in an individual.

The principles of probe selection and array design can readily be extended to analyze more complex polymorphisms (see EP 730,663). For example, to characterize a triallelic SNP polymorphism, three groups of probes can be designed tiled on the three polymorphic forms as described above. As a further example, to analyze a diallelic polymorphism involving a deletion of a nucleotide, one can tile a first group of probes based on the undeleted polymorphic form as the reference sequence and a second group of probes based on the deleted form as the reference sequence.

Arrays can also be designed to analyze many different polymorphisms in many different genes simultaneously simply by including multiple subarrays of probes. Each subarray has first and second groups of probes designed for analyzing a particular polymorphism according to the strategy described above.

For assay of genomic DNA, virtually any biological sample (other than pure red blood cells) is suitable. For example, convenient tissue samples include whole blood, semen, saliva, tears, urine, fecal material, sweat, buccal, skin and hair. Genomic DNA is typically amplified before analysis. Amplification is usually effected by PCR using primers flanking a suitable fragment e.g., of 50–500 nucleotides containing the locus of the polymorphism to be analyzed. The target is usually labelled in the course of amplification. The amplification product can be RNA or DNA, single stranded or double stranded. If double stranded, the amplification product is typically denatured before application to an arrray. If genomic DNA is analyzed without amplification, it may be desirable to remove RNA from the sample before applying it to the array. Such can be accomplished by digestion with DNase-free RNase.

III. Expression Monitoring

The invention monitors the levels of RNA transcripts expressed from genes of interest. The RNA transcript can be nuclear RNA, mRNA, rRNA or tRNA. Nuclear RNA contains intronic sequences that have been spliced out of mRNA. Analysis of nuclear RNA can be useful in analyzing the effects on expression of polymorphisms occurring within intronic regions. In some methods, RNA is monitored directly and in other methods RNA is monitored indirectly via an amplification product, such as cDNA or cRNA.

Strategies for analysis and quantification of transcript are described in detail in commonly owned WO 96/10365 and WO 97/27137. In general, the same probe arrays that are used for analyzing polymorphic forms in genomic DNA can be used for analyzing polymorphic forms of transcript. The hybridization patterns of the probe arrays can be analyzed in the same manner for genomic and RNA (or RNA-derived) targets. Comparison of the hybridization intensities of the first probe group that are perfectly matched with one polymorphic form to the hybridization intensities of the second probe group that are perfectly matched with the second polymorphic form indicates approximately the relative proportions of the polymorphic forms in the transcript.

In some instances, it can be useful to compare the ratio of hybridization intensities of perfectly matched probes from the first and second probe groups for genomic DNA and RNA targets (or amplification products thereof). Preferably, the comparison is performed between like forms of amplification products (i.e., both DNA or both RNa). In genomic DNA from a diploid individual, the polymorphic forms at a heterozygous gene are expected to be present in equal molar ratio. However, in practice, the ratio of hybridization intensities may differ somewhat from the expected molar ratio due to, for example, base-composition effects on hybridization intensity. By comparing the ratios of hybridization intensities for genomic DNA and RNA (or amplification products thereof) to the same groups of probes, factors other than molar ratio of polymorphic forms that might influence hybridization intensities can largely be eliminated from the analysis. If the ratio of hybridization intensities differs significantly for the genomic and RNA targets (or amplification products thereof), then it can be concluded that the polymorphic forms are differently expressed in the transcript.

Some arrays contain additional probes for measuring the level of transcript of a gene without distinguishing between the polymorphic forms. These probes exhibit perfect complementarity to a segment of the gene distil from the polymorphism used to distinguish polymorphic forms. The presence and level of the transcript can be inferred from the hybridization intensities of these probes, optionally relative to control probes lacking complementarity to the target and designed to measure the background level of hybridization intensity.

RNA transcript for analysis is isolated from a biological sample obtained from a biological tissue or fluid in which the gene of interest is expressed. Samples include sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

Methods of isolating total mRNA are described in Chapter 3 of *Laboratory Techniques in Biochemistry and Molecular Biology: Hybridization With Nucleic Acid Probes, Part I. Theory and Nucleic Acid Preparation,* P. Tijssen, ed. Elsevier, N.Y. (1993) and Chapter 3 of *Laboratory Techniques in Biochemistry and Molecular Biology: Hybridization With Nucleic Acid Probes, Part I. Theory and Nucleic Acid Preparation,* P. Tijssen, ed. Elsevier, N.Y. (1993)).

Frequently, it is desirable to amplify RNA prior to hybridization. The amplification product can be RNA or DNA, single-stranded, or double-stranded. In one procedure, mRNA can be reverse transcribed with a reverse transcriptase and a primer consisting of oligo dT and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template result in amplified RNA. Alternatively, cDNA can be amplified to generate double stranded amplicon, and one strand of the amplicon can be isolated, i.e., using a biotinylated primer that allows capture of the undesired strand on streptavidin beads. Alternatively, asymmetric PCR can be used to generate a single-stranded target.

Typically, amplification product is labelled either in the course of amplification or subsequently. If RNA amplification product is to be hybridized simultaneously with genomic DNA, or an amplification product thereof, to an array, then the two targets are differentially labelled. A variety of different fluorescent labels are available. For example, one sample can be labelled with fluorescein and the other with biotin, which can be stained with phycoerythrinstreptavidin after hybridization. Two target samples can be diluted, if desired, prior to hybridization to equalize fluorescence intensities.

Detailed protocols for PCR are provided in *PCR Protocols, A Guide to Methods and Applications,* Innis et al., Academic Press, Inc. N.Y., (1990). Other suitable amplification methods include the ligase chain reaction (LCR) (see Wu and Wallace, *Genomics,* 4: 560 (1989), Landegren, et al., *Science,* 241: 1077 (1988) and Barringer, et al., *Gene,* 89: 117 (1990), transcription amplification (Kwoh, et al., *Proc. Natl. Acad. Sci. USA,* 86: 1173 (1989)), and self-sustained sequence replication (Guatelli, et al., *Proc. Nat. Acad. Sci. USA,* 87: 1874 (1990)). In some methods, a known quantity of a control sequence is co-amplified using the same primers to provide an internal standard that may be used to calibrate the PCR reaction to ensure that the amplification products are produced in approximately the same molar ratio as the starting ratio of templates. The probe array then includes probes specific to the internal standard for quantification of the amplified nucleic acid.

IV. Correlation of Genotype with Expression Levels

Having identified alleles of a gene that are expressed at different levels, the alleles can be further analyzed to identify a difference between them that accounts for the different expression levels. The difference may reside in the same polymorphism that was used to distinguish the different allelic forms in the analyses described above. However, more typically, the difference in expression levels resides in a second polymorphism located in a promoter, enhancer or other regulatory regions. Such polymorphisms can be identified by sequencing the regulatory regions of the differentially expressed alleles and identifying sequence differences between the alleles.

A possible causative role of a polymorphism within a regulatory sequence in differential expression of alleles can be analyzed by both molecular biological and genetic approaches. For example, if differentially expressed alleles differ from each other at a polymorphic site within a promoter, the different forms of the promoter can be cloned and placed in operable linkage with a reporter gene. If the reporter gene is expressed at different levels from the two forms of the promoter, it is likely that the polymorphism within the promoter has a causative role in the observed differential expression levels of allelic forms of the gene with which it is naturally associated. Similar reporter assays can be devised to assess the effect of polymorphisms in other regulatory sequences.

Polymorphisms within promoters and other regulatory sequences can also be characterized by association analysis. Association analysis identifies correlations between polymorphic forms and a population of individuals who have been tested for the presence or absence of a phenotypic trait of interest and for polymorphic markers sets. To perform such analysis, the presence or absence of a polymorphism is determined for a set of the individuals, some of whom exhibit a particular trait, and some of which exhibit lack of the trait. The alleles of the polymorphism are then reviewed to determine whether the presence or absence of a particular allele is associated with the trait of interest. Correlation can be performed by standard statistical methods such as a K-squared test and statistically significant correlations between a polymorphic form and phenotypic characteristics are noted.

V. Alternative Method of Correlating Expression Levels with Genotype

In an alternative or additional approach, a population of individuals is genotyped at one or more polymorphic sites within a gene including flanking sequences. Expression levels of the gene transcript are then determined in individuals without distinguishing between the polymorphic forms. Optionally expression levels from different individuals can be classified into groups or clusters suggested by the data, not defined a priori, such that isolates in a given cluster tend to be similar and isolates in different clusters tend to be dissimilar. See commonly owned USSN 08/797,812, filed Feb. 7, 1997 now U.S. Pat. No. 6,228,575 May 8, 2001 (incorporated by reference in its entirety for all purposes). The population of individuals on which the analysis is performed should preferably be matched for characteristics that might have indirect affects on expression levels such as age, sex and ethnicity, and expression levels should be determined from the same tissue type. The genotype of an individual with respect to one or more polymorphisms within the gene is then correlated with the expression level of gene transcript in the same individual throughout the population. Polymorphic forms showing strong correlation with expression levels of transcript may have a causative role in determining the expression level. This role can be further investigated using the molecular biological and genetic approaches described above.

VI. Association Analysis

Phenotypic traits suitable for association analysis include diseases that have known but hitherto unmapped genetic components (e.g., agammaglobulimenia, diabetes insipidus, Lesch-Nyhan syndrome, muscular dystrophy, Wiskott-Aldrich syndrome, Fabry's disease, familial hypercholesterolemia, polycystic kidney disease, hereditary spherocytosis, von Willebrand's disease, tuberous sclerosis, hereditary hemorrhagic telangiectasia, familial colonic polyposis, Ehlers-Danlos syndrome, osteogenesis imperfecta, and acute intermittent porphyria). Phenotypic traits also include symptoms of, or susceptibility to, multifactorial diseases of which a component is or may be genetic, such as autoimmune diseases, inflammation, cancer, diseases of the nervous system, and infection by pathogenic microorganisms. Some examples of autoimmune diseases include rheumatoid arthritis, multiple sclerosis, diabetes (insulin-dependent and non-independent), systemic lupus erythematosus and Graves disease. Some examples of cancers include cancers of the bladder, brain, breast, colon, esophagus, kidney, leukemia, liver, lung, oral cavity, ovary, pancreas, prostate, skin, stomach and uterus. Phenotypic traits also include characteristics such as longevity, appearance (e.g., baldness, obesity), strength, speed, endurance, fertility, and susceptibility or receptivity to particular drugs or therapeutic treatments.

Such correlations can be exploited in several ways. In the case of a strong correlation between a polymorphic form and a disease for which treatment is available, detection of the polymorphic form set in a human or animal patient may justify immediate administration of treatment, or at least the institution of regular monitoring of the patient. Detection of a polymorphic form correlated with serious disease in a couple contemplating a family may also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic set and human disease, immediate therapeutic intervention or monitoring may not be justified. Nevertheless, the patient can be motivated to begin simple life-style changes (e.g., diet, exercise) that can be accomplished at little cost to the patient but confer potential benefits in reducing the risk of conditions to which the patient may have increased susceptibility by virtue of variant alleles. Identification of a polymorphic set in a patient correlated with enhanced receptiveness to one of several treatment regimes for a disease indicates that this treatment regime should be followed.

VII. Probe Array Design and Construction

VLSIPS™ technology provides methods for synthesizing arrays of many different oligonucleotide probes that occupy a very small surface area. See U.S. Pat. No. 5,143,854 and WO 90/15070. For example, high density arrays can be produced which comprise greater than about 100, preferably greater than about 1000, 16,000, 65,000, 250,000 or 1,000,000 different oligonucleotide probes. The oligonucleotide probes range from about 5 to about 50 or about 5 to about 45 nucleotides, more preferably from about 10 to about 40 nucleotides and most preferably from about 15 to about 40 nucleotides in length. In some embodiments, the oligonucleotide probes are 20 or 25 nucleotides in length. The oligonucleotide probes are usually less than 50 nucleotides in length, generally less than 46 nucleotides, more generally less than 41 nucleotides, most generally less than 36 nucleotides, preferably less than 31 nucleotides, more preferably less than 26 nucleotides, and most preferably less than 21 nucleotides in length. The probes can also be less than 16 nucleotides or less than even 11 nucleotides in length.

The location and sequence of each different oligonucleotide probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The small surface area of the array (often less than about 10 $cm^2$, preferably less than about 5 $cm^2$ more preferably less than about 2 $cm^2$, and most preferably less than about 1.6 $cm^2$) permits uniform hybridization conditions, such as temperature regulation and salt content.

Finally, because of the small area occupied by the high density arrays, hybridization may be carried out in extremely small fluid volumes (e.g., 250 $\mu$l or less, more preferably 100 $\mu$l or less, and most preferably 10 $\mu$l or less). In small volumes, hybridization may proceed very rapidly. In addition, hybridization conditions are extremely uniform throughout the sample, and the hybridization format is amenable to automated processing.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A method of monitoring expression levels of different polymorphic forms of a gene, comprising:

hybridizing genomic DNA or an amplification product thereof from an individual to a first probe group comprising one or more probes exactly complementary to a first polymorphic form of the gene, and a second probe group comprising one or more probes exactly complementary to a second polymorphic form of the gene to determine the presence of heterozygous polymorphic forms at a polymorphic site within a transcribed sequence of a gene of interest;

hybridizing RNA or an amplification product thereof from a tissue of the individual in which the gene is expressed to the first and second groups of probes comparing a genomic DNA hybridization intensity of the first probe group to the second group to determine a genomic hybridization ratio, and comparing an RNA hybridization intensity of the first group to the second group to determine an RNA hybridization ratio, whereby a difference in the genomic DNA and RNA ratios indicates that the polymorphic forms of the gene are expressed at different levels in the individual.

2. The method of claim 1, wherein analyzing genomic DNA comprises amplifying a segment of genomic DNA from a sample and hybridizing the amplified genomic DNA to an array of immobilized probes.

3. The method of claim 1, wherein hybridizing the RNA, comprises reverse transcribing and amplifying mRNA expressed from the gene to produce an amplified nucleic acid and hybridizing the amplified nucleic acid to an array of immobilized probes.

4. The method of claim 3, wherein the amplified nucleic acid is cDNA.

5. The method of claim 1, wherein the genomic DNA, or amplification product, and the RNA, or amplification product, bear different labels and are hybridized simultaneously to the array.

6. The method of claim 1, further comprising after the comparing step sequencing a nontranscribed region of the gene to identify a second polymorphic site in a promoter or enhancer region of the gene.

7. A method of monitoring expression levels of different polymorphic forms of a collection of genes, comprising:

hybridizing genomic DNA, or an amplification product thereof, from an individual to an array of immobilized probes comprising a subarray of probes for each gene in the collection, wherein each subarray comprises a first group of one or more probes exactly complementary to a first polymorphic form of the gene and a second group of one or more probes exactly complementary to a second polymorphic form of the gene;

analyzing the relative hybridization of the first and second group of probes to the genomic DNA or amplification product thereof for each subarray to identify heterozygous genes in the individual;

hybridizing RNA or an amplification product thereof from the individual to the array of immobilized probes;

for each subarray of probes for which a heterozygous gene has been identified in the analyzing step, comparing a genomic DNA hybridization intensity of the first probe group to the second group to determine a genomic hybridization ratio, and comparing an RNA hybridization intensity of the first group to the second group to determine an RNA hybridization ratio, whereby a difference in the genomic DNA and RNA ratios indicates that the polymorphic forms of the gene are expressed at different levels in the individual.

8. The method of claim 7, wherein the collection of genes comprises at least 100 genes.

9. The method of claim 7, wherein the collection of genes comprises at least 1000 genes.

10. The method of claim 7, wherein the collection of genes comprises at least 100,000 genes.

11. The method of claim 7, further comprising sequencing a nontranscribed region of a gene in the collection to identify a further polymorphism in a promoter, enhancer or intronic sequence of the gene.

* * * * *